United States Patent [19]
Akselrod et al.

[11] Patent Number: 5,797,840
[45] Date of Patent: Aug. 25, 1998

[54] APPARATUS AND METHOD FOR TIME DEPENDENT POWER SPECTRUM ANALYSIS OF PHYSIOLOGICAL SIGNALS

[75] Inventors: Solange Akselrod, Ramat Ilan; Laurence Keselbrener, Tel Aviv, both of Israel

[73] Assignee: Ramot University Authority for Applied Research & Industrial Development Ltd.

[21] Appl. No.: 793,583
[22] PCT Filed: Sep. 13, 1995
[86] PCT No.: PCT/US95/11686
    § 371 Date: Feb. 28, 1997
    § 102(e) Date: Feb. 28, 1997
[87] PCT Pub. No.: WO96/08992
    PCT Pub. Date: Mar. 28, 1996

[30] Foreign Application Priority Data

Sep. 14, 1994 [IL] Israel .......................... 110973

[51] Int. Cl.⁶ .................................................. A61B 5/00
[52] U.S. Cl. ................... 600/301; 600/300; 600/483
[58] Field of Search .......................... 600/300, 301, 600/483, 484

[56] References Cited

U.S. PATENT DOCUMENTS

| | | |
|---|---|---|
| 4,510,944 | 4/1985 | Porges . |
| 4,777,960 | 10/1988 | Berger et al. . |
| 4,862,361 | 8/1989 | Gordon et al. ............... 364/413.06 |
| 4,896,675 | 1/1990 | Ohsuga et al. . |
| 4,979,110 | 12/1990 | Albrecht et al. . |
| 5,046,504 | 9/1991 | Albert et al. . |
| 5,143,078 | 9/1992 | Mather et al. . |
| 5,299,119 | 3/1994 | Kraf et al. . |
| 5,590,650 | 1/1997 | Genova . |

*Primary Examiner*—William E. Kamm
*Assistant Examiner*—Carl H. Layno
*Attorney, Agent, or Firm*—Mark M. Friedman

[57] ABSTRACT

An apparatus for time dependent power spectrum analysis of a physiological signal modulated by the autonomic nervous system. The apparatus includes a sensor for picking up a physiological signal modulated by the autonomic nervous system and a frequency selection apparatus for selecting at least one frequency inherent to the signal. The apparatus further includes a selective windowed time-frequency analysis processor for determining the power spectrum of the physiological signal within a window along the signal for the at least one frequency and an output apparatus for providing information associated with the functioning of the autonoinic nervous system as provided by the power spectrum of the physiological signal.

50 Claims, 6 Drawing Sheets

APPARATUS AND METHOD FOR TIME DEPENDENT POWER SPECTRUM ANALYSIS OF PHYSIOLOGICAL SIGNALS

FIELD AND BACKGROUND OF THE INVENTION

The present invention relates to apparatus and method for time dependent power spectrum analysis of physiological signals in general and in particular to time dependent power spectrum analysis of cardio-respiratory physiological signals modulated by the Autonomic Nervous System (ANS).

It is well known that many physiological signals are modulated by the Autonomic Nervous System (ANS). Such physiological signals include cardio-respiratory signals including, respiration, ECG, heart rate (HR), blood pressure (BP), blood flow, vascular resistance, cardiac volume, cardiac cross section, cardiac contractility, peripheral resistance, and the like. Other physiological signals which are not modulated by the ANS include EEG signals, EMG signal, ECoO signals, and the like.

It is also well known that perturbations and/or transient chances which affect the functioning of the ANS affect the physiological signals and vice versa. Common perturbations used in the analysis of autonomic control include changing of posture, tilt, pharmaceutical interventions, deep breaths, vacal maneuvers, hand grip, and others.

Generally speaking, the power spectrum of physiological signals in humans modulated by the ANS can be divided into two frequency ranges: the Low Frequency (LF) range below 0.15 Hz and the High Frequency (HF) range above 0.15 Hz displaying a peak at about 0.2 Hz for adults and a peak at about 0.4 Hz for children. The HF range is mediated by the fast reacting parasympathetic nervous system while the LF range is mediated by both the parasympathetic nervous system and the slower reacting sympathetic nervous system.

Standard spectral analysis by Fourier transform or variations of Auto-Regressive Models have been extensively applied in an attempt to evaluate physiological signals quantitatively under steady state conditions. However, these approaches limit the analysis to rest or restabilization conditions and are not suitable for fast or transient responses which negate the assumption of stationarity.

More recently, approaches have been developed which overcome the stationarity limitations of standard spectral analysis. These approaches can be classified into two main groups: time frequency distributions and time dependent models. Time frequency distributions include the Short Time Fourier Transform (STFT), distributions belonging to the Cohen's class such as the Wigner-Ville Distribution (WVD), Exponential Distribution (ED), and the like. Time dependent models are based on Auto Regressive (AR) or Auto Regressive Moving Average (ARMA) modeling. The disadvantages of the above described approaches include the compromise between frequency resolution and quasi-stationarity for the STFT, the smoothing required by WVD to remove interference terms, the importance of the empirically chosen forgetting factor and the model order of the time dependent AR and ARMA models.

A still more recent advance in the analysis of time dependent signals is described in a paper entitled "The Wavelet Transform, Time Frequency Localization and Signal Analysis" by I. Daubaechies, IEEE Transactions on Information Theory, Vol. 36, No. 5, September 1990 which is incorporated herein be reference as if set forth fully herein. However, up to the present time, this approach has been limited to EEG signals as described in an article entitled "EEG Paroxysmic Activity Detected by Neural Networks after Wavelet Transform Analysis" by Clochon et al. in the European Symposium on Artificial Neural Networks (ESANN) 1993 Proceedings, pg 145–150.

There is therefore a need for apparatus and method for time dependent power spectrum analysis of physiological signals in general and of cardio-respiratory physiological signals modulated by the Autonormic Nervous System (ANS) in particular which overcome the above-mentioned deficiencies.

SUMMARY OF THE INVENTION

The present invention is for an apparatus and method for time dependent power spectrum analysis of physiological signals in general and of cardio-respiratory physiological signals modulated by the Autonomic Nervous System (ANS) in particular.

Hence, there is provided according to a first aspect of the present invention, an apparatus for time dependent power spectrum analysis of a physiological signal modulated by the autonomic nervous system, the apparatus comprising: (a) a sensor for picking up a physiological signal modulated by the autonomic nervous system; (b) frequency selection apparatus for selecting at least one frequency inherent to the signal; (c) a selective windowed time-frequency analysis processor for determining the power spectrum of the physiological signal within a window along the signal for the at least one frequency; and (d) output apparatus for providing information associated with the functioning of the autonomic nervous system as provided by the power spectrum of the physiological signal.

According to a further feature of the present invention, the sensor is selected from one of the following: an ECG recorder, a respiratory monitor, a blood pressure transducer, a Doppler flow meter, a tachometer, a finger plethysmograph, a skin resistance galvanometer or any other cardiovascular monitoring equipment.

According to a still further feature of the present invention, the window has an aperture selected from one of the following: a rectangular aperture, a Hamming aperture, a Hanning aperture, a Blackman aperture, a Gaussian window, a Lorentzian window, a sinc window, any power of a sine window and any power of a cosine window, or any derivative of these windows.

According to a yet still further feature of the present invention, the apparatus further comprising frequency selection apparatus for determining the frequency resolution of the apparatus.

According to a yet still further feature of the present invention, the apparatus further comprising timing selection apparatus for determining the time resolution of the apparatus.

According to a yet still further feature of the present invention, the apparatus further comprising a physiological signal selector for selecting the type of physiological signal picked up the sensor.

According to a yet still further feature of the present invention, the apparatus further comprising a type of perturbation selector for selecting the type of perturbation to be applied to a subject under investigation.

According to a yet still further feature of the present invention, the apparatus further comprising frequency selection apparatus for determining the range of frequency outputted on the output apparatus.

According to a yet still further feature of the present invention, the apparatus further comprising timing selection apparatus for determining the onset and termination of the time-dependent power spectrum of the physiological signal outputted on the output apparatus.

According to a yet still further feature of the present invention, the apparatus further comprising a detrending filter deployed between the sensor and the selective windowed time-frequency analysis processor.

According to a yet still further feature of the present invention, the selective windowed time-frequency analysis processor is a Wavelet processor.

According to a yet still further feature of the present invention, the apparatus further comprising a prototype function selector for selecting a prototype function applied by the Wavelet processor.

According to a yet still further feature of the present invention, the apparatus further comprising a scale parameters selector for selecting scale parameters applied by the Wavelet processor.

According to a yet still further feature of the present invention, the apparatus further comprising a shift parameters selector for selecting shift parameters applied by the Wavelet processor.

According to a yet still further feature of the present invention, the selective windowed time-frequency analysis processor is a selective discrete spectral transform algorithm processor.

According to a yet still further feature of the present invention, the apparatus further comprising a spectral transform selector for selecting a transform selected from one of the following: the Fourier transform, the Haar transform, the Hartley transform, the sine transform, the cosine transform, and the Hadamard transform.

According to a yet still further feature of the present invention, the apparatus further comprising a window duration selector for selecting the duration of the window.

According to a yet still further feature of the present invention, the apparatus further comprising a window aperture selector for selecting the aperture of the window.

According to a yet still further feature of the present invention, the apparatus further comprising a number of points selector for selecting the number of data points within the window.

According to a yet still further feature of the present invention, the apparatus further comprising a decimation technique selector for selecting the decimation technique applied by the selective discrete spectral transform analysis processor.

There is also provided according to a second aspect of the present invention, a method of time dependent power spectrum analysis of a physiological signal modulated by the autonomic nervous system, the method comprising the steps of: (a) picking up a physiological signal modulated by the autonomic nervous system; (b) selecting at least one frequency inherent to the signal; (c) determining the power spectrum of the physiological signal within a window along the signal for the at least one frequency; and (d) providing information associated with the functioning of the autonomic nervous system as provided by the power spectrum of the physiological signal.

There is further provided according to a third aspect of the present invention, an apparatus for time dependent power spectrum analysis of a physiological signal, the apparatus comprising: (a) a sensor for picking up a physiological signal; (b) a frequency selector for selecting at least one frequency inherent to the signal; (c) window generating apparatus for generating a window along the signal, the duration of the window being substantially inversely related to the at least one frequency; (d) decimation apparatus for providing data points within the window; (e) spectral transform apparatus for determining the power spectrum of the signal within the window for the at least one frequency; and (f) output apparatus for providing information associated with time dependent power spectrum of the signal.

According to a further feature of the present invention, the sensor is selected from one of the following: an ECG recorder, a respiratory monitor, a finger plethysmograph, a Doppler flow meter, a tachometer, a blood pressure transducer, a skin resistance galvanometer, an EEG monitor and an EMG monitor.

According to a still further feature of the present invention, the window having an aperture selected from one of the following: a rectangular aperture, a Hamming aperture, a Hanning aperture, a Blackman aperture, a Gaussian window, a Lorentzian window, a sinc window, any power of a sine window and any power of a cosine window or any derivative of these windows.

According to a yet still further feature of the present invention, the apparatus further comprising frequency selection apparatus for determining the frequency resolution of the apparatus.

According to a yet still further feature of the present invention, the apparatus further comprising timing selection apparatus for determining the time resolution of the apparatus.

According to a yet still further feature of the present invention, the apparatus further comprising a physiological signal selector for selecting the type of physiological signal picked up the signal.

According to a yet still further feature of the present invention, the apparatus further comprising a type of perturbation selector for selecting the type of perturbation to be applied to a subject under investigation.

According to a vet still further feature of the present invention, the apparatus further comprising frequency selection apparatus for determining the range of frequency outputted on the output apparatus.

According to a yet still further feature of the present invention, the apparatus further comprising timing selection apparatus for determining the onset and termination of the time dependent power spectrum of the physiological signal outputted on the output apparatus.

According to a yet still further feature of the present invention, the apparatus further comprising a detrending filter deployed between the sensor and the selective windowed time-frequency analysis processor.

According to a yet still further feature of the present invention, the apparatus further comprising a spectral transform selector for selecting a transform selected from one of the following: the Fourier transform, the Haar transform, the Hartley transform, the sine transform, the cosine transform, and the Hadamard transform.

According to a yet still further feature of the present invention, the apparatus further comprising a window duration selector for selecting the duration of the window.

According to a yet still further feature of the present invention, the apparatus further comprising a window aperture selector for selecting the aperture of the window.

According to a yet still further feature of the present invention, the apparatus further comprising a number of points selector for selecting the number of data points within the window.

According to a yet still further feature of the present invention, the apparatus further comprising a decimation technique selector for selecting the decimation technique applied by the selective discrete spectral transform analysis processor.

There is still further provided according to a fourth aspect of the present invention, a method of time dependent power spectrum analysis of a physiological signal, the method comprising the steps of: (a) picking up a physiological signal; (b) selecting at least one frequency inherent to the signal; (c) generating a window alone the signal, the duration of the window being substantially inversely related to the at least one frequency; (d) providing data points within the window; (e) determining the power spectrum of the signal within the window for the at least one frequency; and (f) providing information associated with time dependent power spectrum of the signal.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of an apparatus and method for time dependent power spectrum analysis of physiological signals in general and of cardio-respiratory physiological signals modulated by the Autonomic Nervous System (ANS) in particular.

The principles and operation of the apparatus and method according to the present invention may be better understood with reference to the drawings and the accompanying description.

Figure 1A:
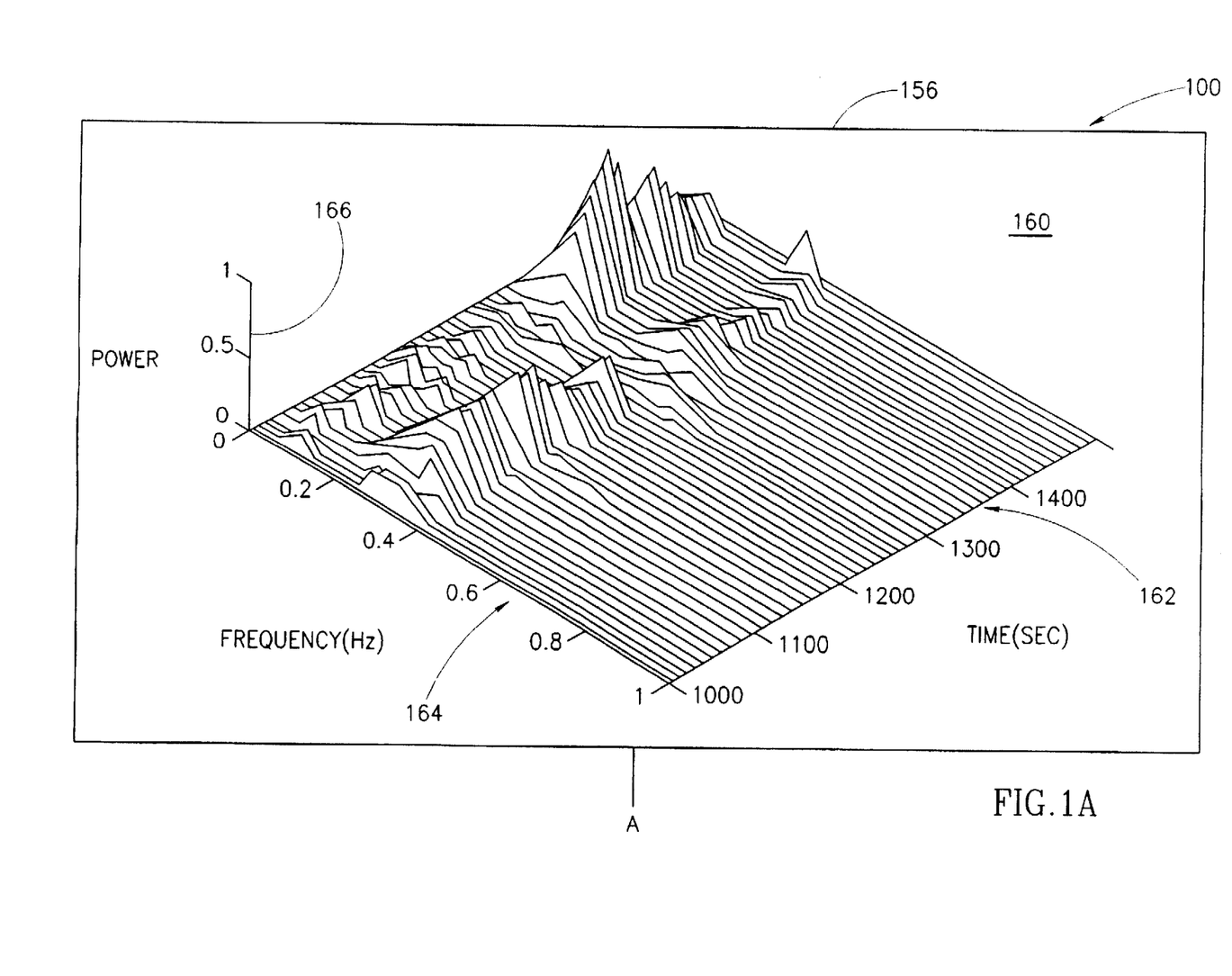
FIGS. 1A and 1B are is a block diagram of a preferred embodiment of an apparatus, constructed and operative according to the teachings of the present invention, employing a selective windowed time-frequency analysis processor for time dependent power spectrum analysis of physiological signals.
Figure 1B:
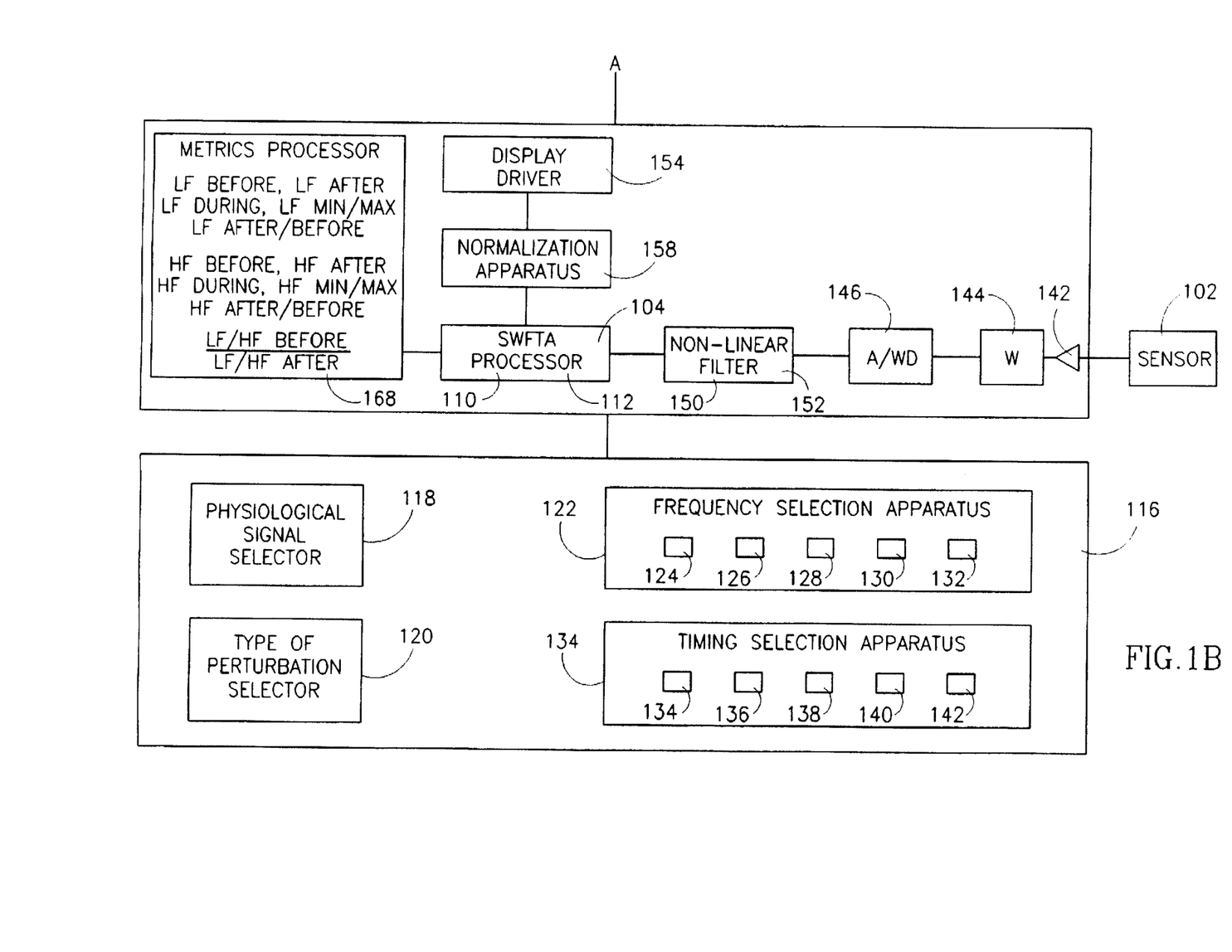

Referring now to the drawings, FIG. 1B shows an apparatus, generally designated 100, constructed and operative according to the teachings of the present invention, for analyzing the time dependent power spectrum of physiological signals in general and cardio-respiratory physiological signals modulated by the autonomic nervous system (ANS) in particular.

Generally speaking, apparatus 100 performs time dependent power spectrum analysis of a stationary or a non-stationary, mono-component or multi-component physiological signal picked-up by a sensor 102 adapted for detecting the physiological signal. The physiological signals include cardio-respiratory signals including, respiration, ECG, heart rate (HR), blood pressure (BP), blood flow, vascular resistance, cardiac volume, cardiac cross section, cardiac contractility, peripheral resistance, and the like. Other physiological signals which are not modulated by the ANS include EEG signals, EMG signal, ECoG signals, and the like. Hence, sensor 102 can be an ECG recorder, a respiratory monitor, a blood pressure transducer, a Doppler flow meter, a tachometer, a finger plethysmograph, a skin resistance galvanometer, a skin resistance galvanometer, cadiovascular monitoring equipment, and the like.

Figure 2:
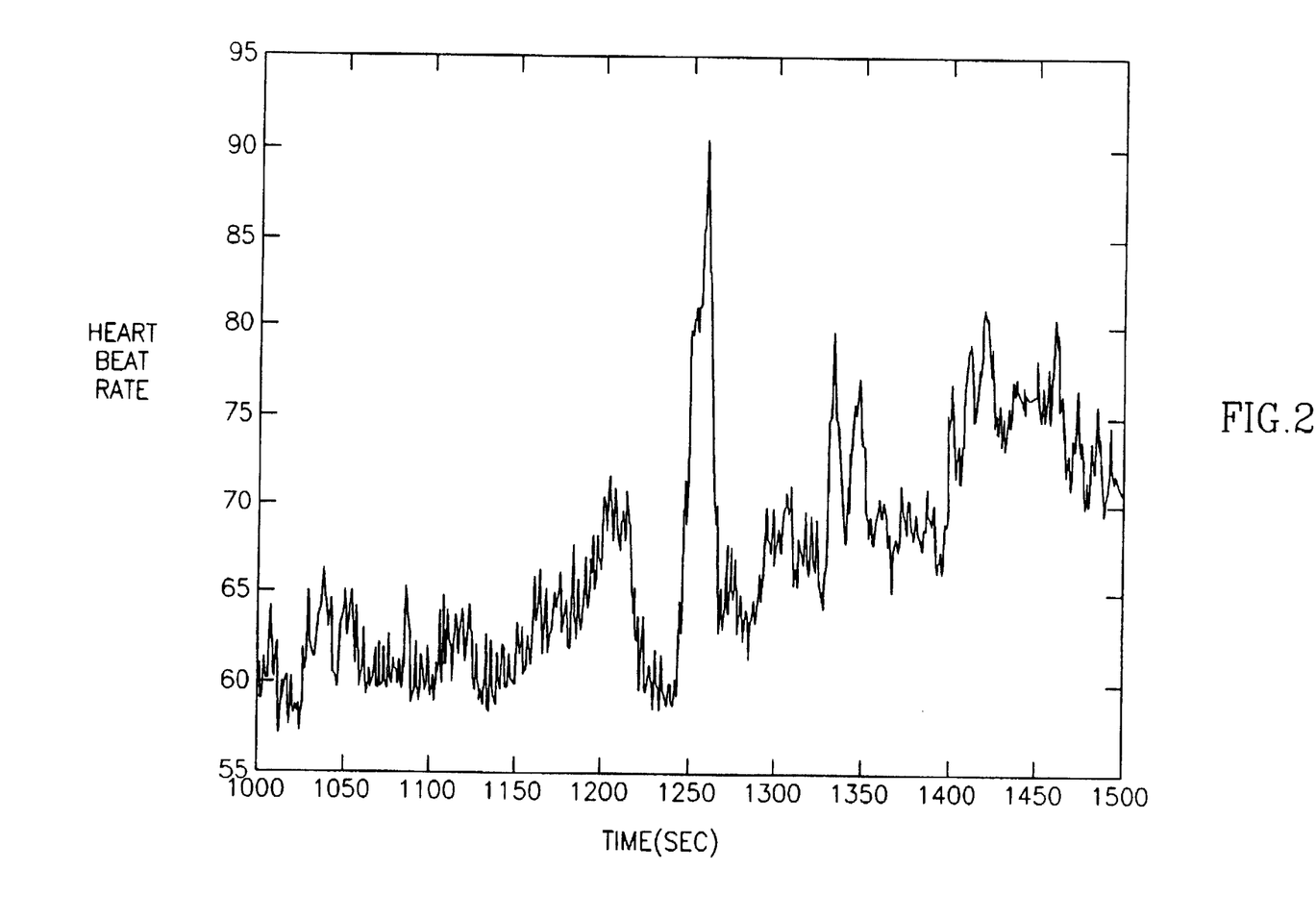
FIG. 2 is a representative trace of the heart rate detected from an ECG signal picked up by an ECG recorder of a subject who undergoes a perturbation in the form of a change in posture from a supine position to a standing position.

For the sake of exposition, FIG. 2 depicts a representative trace of the heart rate as detected from an ECG signal as picked up by an ECG recorder of a human subject undergoing a perturbation in the form of a change in posture (CP) at about time t=1225 seconds to be analyzed by apparatus 100. As is well known, a change in posture (CP) induces an increase in the heart rate of the subject. The increase in heart rate is caused by changes in the modulation of the heart rate by both branches of the autonomic nervous system. First, by an attenuation in the modulation exerted by the fast reacting parasympathetic nervous system. And second, by the strengthening in the modulation of the heart rate exerted by the slower reacting sympathetic nervous system.

The attenuation in the modulation of the heart rate exerted by the parasympathetic nervous system is typically manifested by a sudden overshoot in the heart rate just after the perturbation and then a gradual increase in heart rate such that the average heart rate is greater after the perturbation than before the perturbation. The strengthening in the modulation of the heart rate exerted by the slower reacting sympathetic nervous system is manifested by the gradual increase in the average heart rate from about 1300 seconds to about 1500 seconds.

It is a particular feature of the present invention that apparatus 100 includes a selective windowed time-frequency analysis (SWTFA) processor, generally designated 104, for providing the time-dependent power spectrum analysis of the physiological signal picked up by sensor 102. SWTFA processor 104 can be realized by several implementations including, but not limited to, a Wavelet processor 105 as described in greater detail hereinbelow with reference to FIG. 3, a Selective Discrete Spectral Transform Analysis processor 108 as described in greater detail hereinbelow with reference to FIG. 4, and the like.

In both cases, SWTFA processor 104 includes a window generator 106 for generating a series of windows along the signal within which the power spectrum of the frequencies under investigation is to be analyzed. Furthermore, SWTFA processor 104 includes a power spectrum determination apparatus 112 for determining the power spectrum for a particular frequency within each window provided by window generator 110. Depending on the particular implementation of SWTFA processor 104, the aperture of the windows can be, but are not limited to, a rectangular aperture, a Hamming aperture, a Blackman aperture, a Gaussian window, a Lorentzian window, a sinc window, any power of a sine window, any power of a cosine window, any derivative of these windows, and the like.

It is a particular feature of SWTFA processor 104 that the duration of the windows is generally inversely proportional to the frequency under investigation. Hence, low frequencies are investigated using long time windows while high frequencies are investigated using short time windows. It is a further feature of SWTFA processor 104 that a physiological signal can be analyzed at a wide range of both frequency resolutions and time resolutions. Typically, SWTFA processor 104 is capable of a frequency resolution in the order of 0.001 Hz at the low frequency end of the spectrum for, say, a duration of 30 minutes or even lower for a longer time duration. Furthermore, SWTFA processor 104 is capable of a time resolution which can reach I second for frequencies of around 2 Hz. The time and frequency resolutions reach intermediate values around the center of the time-frequency plane.

To regulate the function of SWTFA processor 104, apparatus 100 includes an operator interface 116 enabling an operator to select the type of physiological signal to be analyzed, the type of perturbation, and other operating parameters as will be described hereinbelow. Hence, operator interface 116 includes a physiological signal selector 118 for selecting the type of physiological signal to be analyzed and a type of perturbation selector 120 for selecting the type of perturbation to be applied to a subject under investigation.

The frequencies or ranges of frequencies under investigation are preferably selected by a user using frequency selection apparatus 122. Typically, one or more frequencies can be selected for investigation from a range from about 0 Hz and about 20 Hz for the analysis of the autonomic nervous systems of a wide range of mammals. The frequencies under investigation are determined by assigning values to a first frequency register 124, a last frequency register 126 and a frequency interval register 128 such that SWTFA processor 104 processes a sequence of frequencies starting at the first frequency stored in first frequency register 124 and increasing in steps determined by frequency interval resister 128 up to the last frequency stored in last frequency register 126. Furthermore, frequency selection apparatus 122 preferably includes one or more frequency range selectors 130 and 132 for determining the display of their corresponding power spectrum. Typically, frequency range selectors 130 and 132 are used for selecting displays of LF power and HF power.

Operator interface 116 also includes timing selection apparatus 134 which includes a timer 136 for determining the time resolution of the analysis of the physiological signal and several pairs of START and STOP timers as described hereinbelow. It should be noted that timer 136 determines the degree of overlapping between consecutive windows. A first pair of timers 138 is preferably dedicated to controlling the onset and termination of the display of the LF power spectrum of the autonomic control modulating the physiological signal. A second pair of timers 140 is preferably dedicated to controlling the onset and termination of the display of the HF power spectrum of the autonomic control moderating the physiological signal. Other timers 142 can be assigned by the operator to determine time intervals during which other parameters can be displayed or calculated.

SWTFA processor 104 is typically connected to sensor 102 via an amplifier 142, an anti aliasing filter 144, and an A/D converter 148. Other devices may be required to provide suitable data to SWTFA processor 104 depending on the type of signal being picked up by sensor 102. For example, in the case of sensor 102 picking up heartbeats, then an R wave detector is required to provide suitable data to SWTFA processor 104. The additional devices required to be provide suitable data to SWTFA processor 104 can be connected through selection of the type of physiological sensor to be picked up by sensor 102 using physiological signal selector 118.

It is a further feature of the present invention that apparatus 100 preferably includes a detrending filter 150 deployed between A/D converter 146 and SWTFA processor 104 such that sudden changes of amplitude in the physiological signal after the perturbation do not affect the natural high frequency components of the physiological signal. The parameters of detrending filter 150 can be determined by the settings of physiological signal selector 118 and type of perturbation selector 120. Alternatively, the parameters of detrending filter 150 can be set by the operator using detrending filter control 152.

Apparatus 100 further includes a display driver 154 for providing output on an output apparatus realized as a display monitor 156 and a normalization apparatus 158 for normalizing the output on display monitor 156. Output apparatus can also include a printer. The displays can include 3D graphic displays, 2D contour map displays, time dependent oscilloscope type displays, and the like depending on the type of information required by an operator. In particular, display driver 154 can display a 3D time dependent power spectrum graph 160 where the x-axis 162 of graph 160 depicts frequency in Hz, the y-axis 164 of graph 160 depicts time in seconds and the z-axis 166 of graph 160 depicts the power spectrum in units associated with the type of physiological signal being picked up by sensor 102. For example, z-axis 166 can have units of beats per minute$^2$ Hz$^{-1}$ (BPM$^2$ Hz$^{-1}$) when the physiological signal measured is heart beat, mmHg$^2$ Hz$^{-1}$ when the physiological signal measured is blood pressure, (mlsec$^{-1}$)$^2$ Hz$^{-1}$ when the physiological signal measured is blood flow, and the like.

Furthermore, apparatus 100 includes a metrics processor 168 for providing one or more metrics depending on the type of information required by an operator. Metrics processor 168 typically receives input from a number of sources including, but not limited to, physiological signal selector 118, type of perturbation selector 120, frequency selection apparatus 122, timing selection apparatus 134, and the like. Hence, metrics processor 168 can provide the baseline LF power before perturbation, the LF power during or after perturbation, maximal and/or minimal activity during perturbation and the ratio therebetween. In a similar fashion, metrics processor 168 can provide the baseline HF power before perturbation, the HF power during or after perturbation, maximal and/or minimal activity during perturbation and the ratio therebetween. Still further, metrics processor 168 can provide the LF/HF ratio before perturbation to the LF/HF ratio after perturbation.

Figure 3:
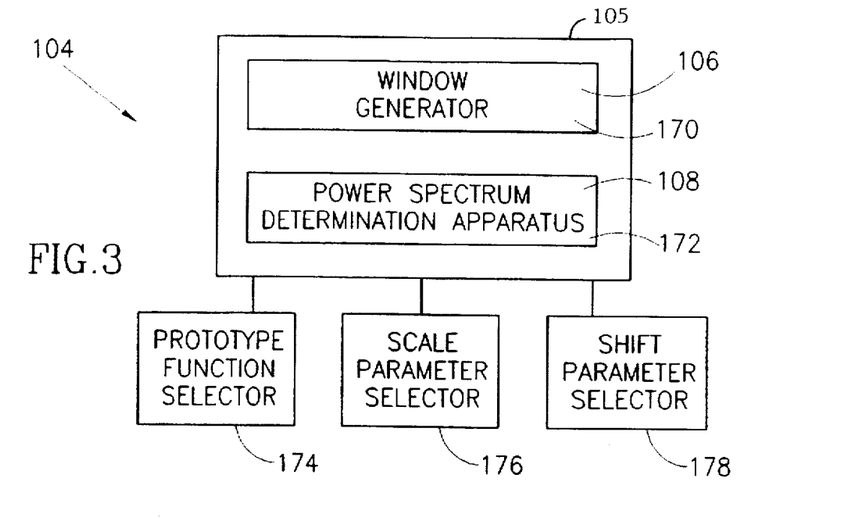
FIG. 3 is a block diagram of the selective windowed time-frequency analysis processor of FIG. 1 realized as a wavelet processor.

With reference now to FIG. 3, the block diagram depicts the preferred embodiment of SWTFA processor 104 realized as Wavelet processor 105 including window generator 106 additionally designated 170 and power spectrum determination apparatus 108 additionally designated 172. For further information on wavelet processing, reference is made to the aforementioned paper entitled "The Wavelet Transform, Time Frequency Localization and Signal Analysis" by I. Daubaechies, IEEE Transactions on Information Theory, Vol. 36, No. 5, September 1990 which is incorporated herein be reference as if set forth fully herein.

Broadly speaking, the aperture, duration and the time resolution between consecutive windows provided by window generator 170 are defined by three parameters: a prototype function h(t), a scale parameter "a" and a shift parameter "b" according to the Wavelet transform:

$$\int h_{a,b}(t)\, f(t) \cdot dt \text{ where } a \in R^+, b \in R$$

As well known in the art, for a large scale parameter value, the prototype function is stretched such that the prototype Wavelet acts as a low frequency function while, for a small scale parameter value, the prototype function is contracted such that the Wavelet function acts a high frequency function. Hence, depending on the value assigned to scaling parameter "a", the Wavelet function dilates or contracts in time, causing the corresponding contraction or dilation in the frequency domain. Thus, the Wavelet transform provides a flexible time-frequency resolution and analyzes higher frequencies with better time resolution but poorer frequency resolution than lower frequencies.

Preferably, apparatus 100 is configured such that the settings of physiological signal selector 118 and type of perturbation selector 120 determine the selections of prototype function h(t), effective scale parameters "a" and effective shift parameters "b", thereby obviating the need for direct operator intervention. Alternatively, apparatus 100 can include a prototype function selector 174 for selection of the prototype function h(t), a scale parameters selector 176 for selection of the scale parameter "a" and a shift parameters selector 178 for selection of shift parameter "b", thereby enabling operator intervention in the regulation of Wavelet processor 105 according to the type of physiological signal to be analyzed, the type of perturbation, and the like. Depending on the prototype function selected, the aperture of the windows can be, but are not limited to, a rectangular aperture, a Hamming aperture, a Blackman aperture, a Gaussian window, a Lorentzian window, a sinc window, any power of a sine window, any power of a cosine window, any derivative of these windows, and the like.

Figure 4:
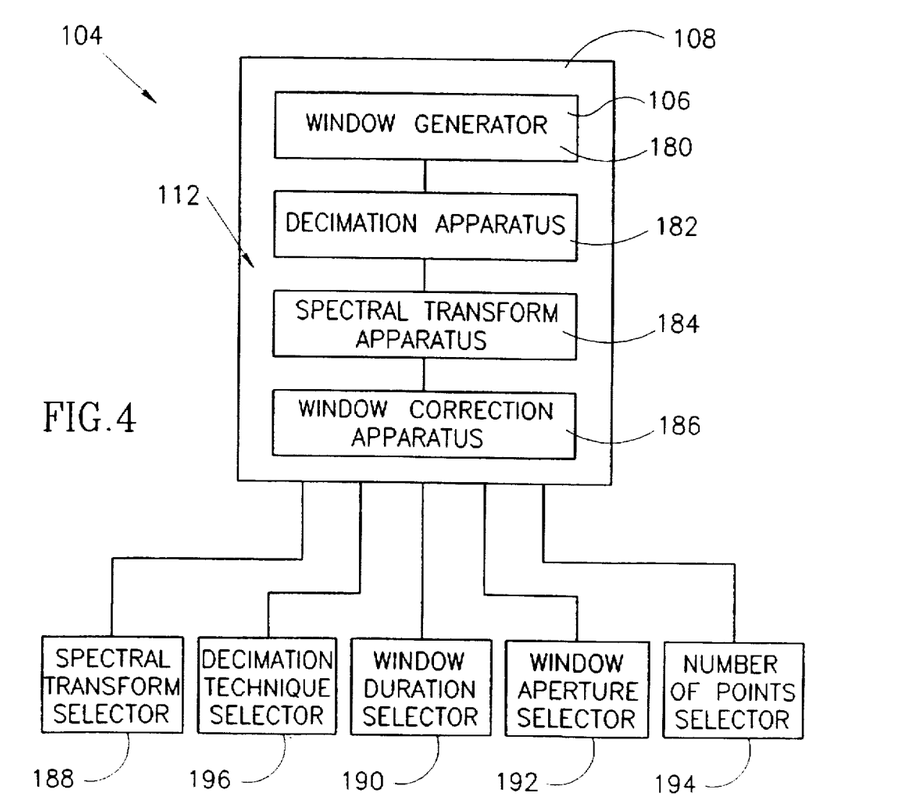
FIG. 4 is a block diagram of the selective windowed time-frequency analysis processor of FIG. 1 realized as a selective discrete spectral transform processor.

With reference now to FIG. 4, the block diagram depicts the preferred embodiment of SWTFA processor 104 realized as Selective Discrete Spectral Transform Algorithm processor (SDA) 108 including window generator 106 additionally designated 180 and power spectrum determination apparatus 112. In this case, power spectrum determination apparatus 112 includes decimation apparatus 182 for providing a constant number of data points from the windows, a spectral transform apparatus 184 for providing the power spectrum of the frequency within the windows based on the data points and a window correction apparatus 186 for correcting the power spectrum due to distortions rendered by window generator 180.

SDA apparatus 108 can employ any one of a number of known transforms for determining the power spectrum of a time dependent physiological signal. Such transforms include the Fourier transform, the Haar transform, the Hartley transform, the sine transform, the cosine transform, the Hadamard transform, and the like. The selection of the spectral transform realized by SDA apparatus 180 is preferably operator controlled by means of a spectral transform selector 188.

As mentioned hereinabove, the duration of windows is preferably inversely related to the frequency under investigation. Depending on the type of signal, the duration of windows typically lies from about 2 periods and about 10 periods of the frequency under investigation. The duration is preferably user selected by means of a window duration selector 190. Alternatively, the duration of the window can be automatically set according to the SNR or similar metric of the physiological signal.

The windows can have different apertures including, but not limited to, a rectangular aperture, a Hamming aperture, a Hanning aperture, a Blackman aperture, a Gaussian window, a Lorentzian window, a sinc window, any power of a sine window, any power of a cosine window, any derivative of these windows, and the like. The aperture of the window is preferably user selected by means of a window aperture selector 192. In the case that spectral transform apparatus 184 employs the Fourier transform and a rectangular window is employed to ensure the highest possible frequency resolution by minimizing side lobes, then window correction apparatus 186 is required to correct the obtained power spectra by dividing by the corresponding sinc function. For other windows and transforms, the correction required depends on the type of window and the mathematical rules of the transform.

Decimation apparatus 182 preferably provides data points by employing a low pass filter and undersampling technique including, but not limited to, moving, average. Typically, decimation apparatus 182 provides the same number of data points irrespective of the duration of the windows so as not to generate artifacts or normalization problems. The number of data points determined in a window is preferably operator selected by means of a number of data points selector 194. Furthermore, SDA apparatus 108 preferably includes a decimation technique selector 196 for selecting a technique for decimation of a window.

In a similar manner to Wavelet processor 106, SDA apparatus 108 can be configured such that settings of physiological signal selector 118 and type of perturbation selector 118 determines: the settings of spectral transform selector 188, window duration selector 190, window aperture selector 192, number of data points selector 194 and decimation technique selector 196.

The operation of apparatus 100 is now described with reference to the time dependent power spectrum analysis of the physiological signal depicted in FIG. 2 of the heart rate of a human subject who has undergone a perturbation in the form of a change of posture at time t=1225 seconds. Hence, an operator selects an appropriate sensor 102, in this case an ECG recorder, for detecting the heart rate of a subject.

Then the operator employs the above-mentioned selectors in the following fashion. First, the operator employs physiological signal selector 118 for selecting the type of physiological signal to be analyzed and perturbation selector 120 for selecting the type of perturbation to be applied to a subject under investigation. These selections can cause connection of an R wave detector if required and the setting of SWTFA processor 104 as described hereinabove. And second, the operator employs frequency selection apparatus 122 to determine the frequencies under investigation by assigning values to registers 124, 126 and 128.

In the case that SWTFA processor 104 is realized as Wavelet processor 105, the operator can employ prototype function selector 174, scale parameters selector 176 and shift parameters selector 178 for setting the prototype function, the scale parameters and the shift parameters of the Wavelet processor 105, respectively. While in the case that SWTFA processor 104 is realized as SDA processor 108, the operator employs spectral transform selector 188, window duration selector 190, window aperture selector 192, number of data points selector 194 and decimation technique selector 196 to determine the settings of SDA apparatus 108.

Apparatus 100, and in particular SWTFA processor 104, analyzes the physiological signal in the following manner. Window generator 110 generates a window toward the onset of the pick-up of the physiological signal for the first frequency under investigation according to the selection of the operator. Power spectrum determination apparatus 112 determines the power spectrum of the frequency within the window and provides the output to both display driver 154 and metrics processor 168. In the same manner, SWTFA processor 104 analyzes the window for other frequencies under investigation according to the selection of the operator such that apparatus 100 provides a real time, time dependent, power spectrum analysis of the physiological signal. It should be noted as described hereinabove that the size of the windows varies as a function of the frequency under investigation. After determining the power spectrum within the window for each frequency under investigation, SWTFA processor 104 repeats the method for the second window deployed forward along the physiological signal according to the time resolution and frequency resolution set by the operator for the next frequency and so on. Alternatively, SWTFA processor 104 can process all the time signal for each frequency under investigation.

With particular reference to SDA processor 108, window generator 180 generates a first window starting at the onset of the pick-up of the physiological signal for the first frequency under investigation according to the selection of the operator, decimation apparatus 182 decimates the data points in the window to provide the predetermined number of data points, spectrum transform apparatus 184 determines the power spectrum of the frequency during the first window and provides the output to window correction apparatus 186 for correction of the power spectrum.

Figure 5A:
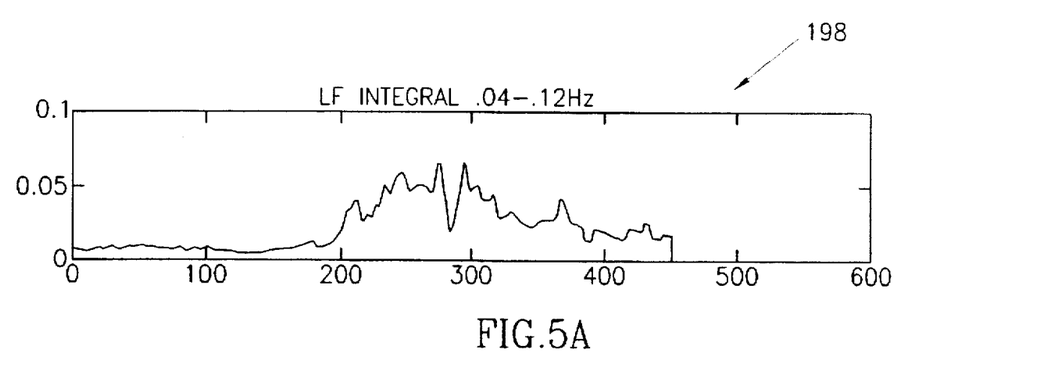
FIGS. 5a–5c are oscilloscope type time dependent graphs of the LF power, the HF power and the LF/HF ratio of the heart rate fluctuations of FIG. 2, respectively.
Figure 5B:
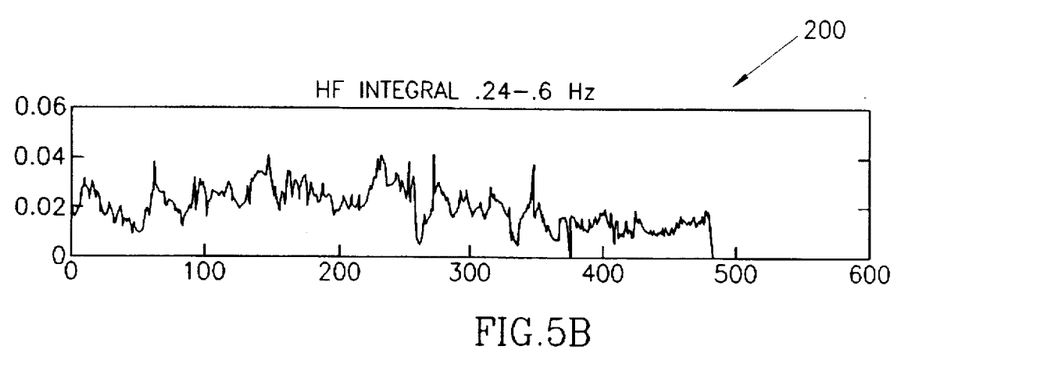
Figure 5C:
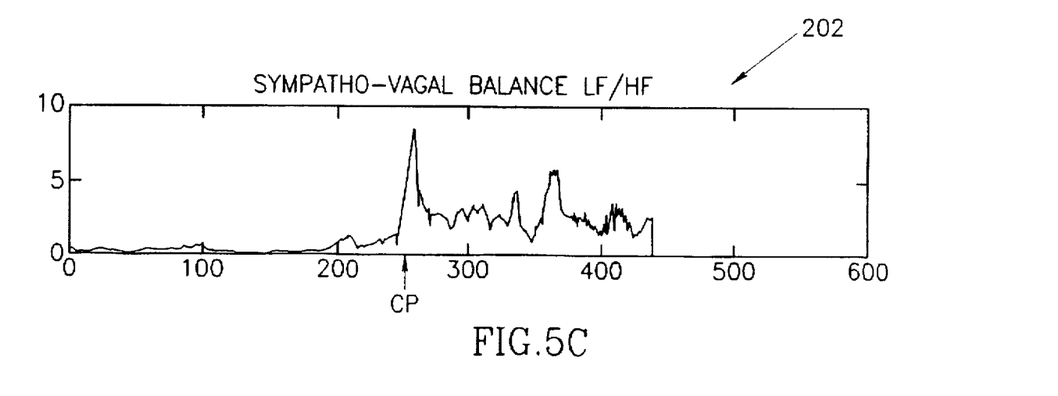
Figure 6:
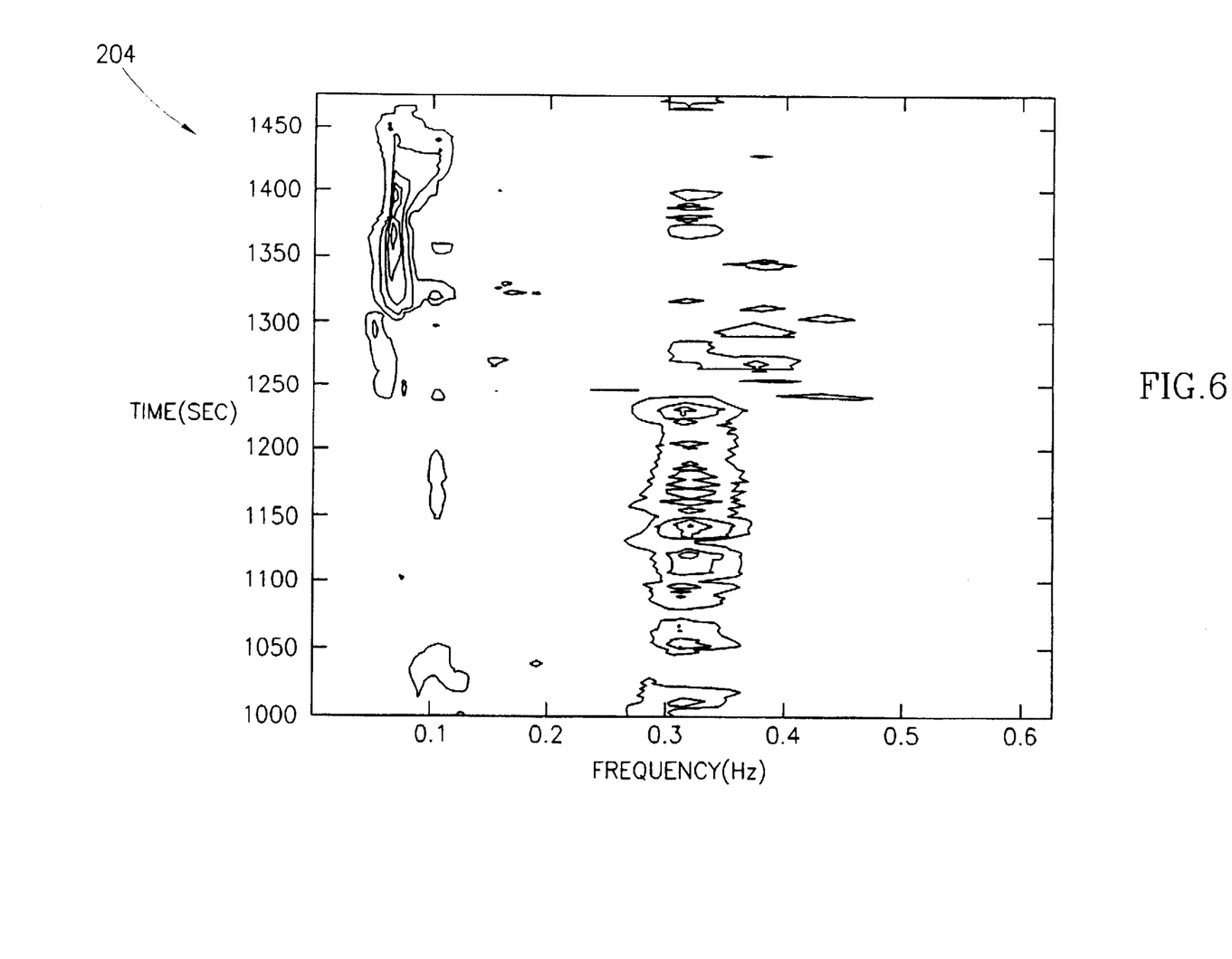
FIG. 6 is a 2D time dependent power spectrum contour map of the 3D time dependent power spectrum graph shown in FIG. 1B.

With reference now to FIGS. 5a-5c, apparatus 100 provides the following displays and metrics after the time dependent power spectrum analysis of the physiological signal shown in FIG. 2. First, display driver 154 can provide an oscilloscope type time dependent LF power graph 198 according to input received from timing selection apparatus 122 and frequency selection apparatus 134. In this case, as shown in FIG. 5a, time dependent LF power graph 198 is provided for the LF power integral over the range of from about 0.04 Hz to about 0.12 Hz. Second, display driver 154 can provide an oscilloscope type time dependent HF power graph 200 according to input received from timing selection apparatus 122 and frequency selection apparatus 134. In this case, as shown in FIG. 5b, time dependent HF power graph 200 is provided for the HF power spectrum integral over the range of from about 0.24 Hz to about 0.6 Hz. Third, display driver 154 can provide an oscilloscope type graph 202 of the sympatho-vagal balance LF/HF as shown in FIG. 5c. Fourth, display driver 154 can display a 2D time dependent power spectrum contour map 204 of time against frequency as shown in FIG. 6 in which the contours are representative of the time dependent power spectrum of the fluctuations of the physiological signal by the autonomic nervous system. And fifth, display driver 154 can provide 3D time dependent power spectrum graph 160 as shown in FIG. 1B. It should be noted that 2D time dependent power spectrum contour map 204 is in fact a top view of 3D time dependent power spectrum graph 160.

Hence, it can be readily appreciated that apparatus 100 provides information regarding the heart rate of the subject as induced by the functioning of the autonomic nervous system due to the change of posture as will now be described in greater detail. First, HF power graph 200 depicts that a sudden attenuation in HF power at the time of perturbation corresponding to the fast response of the parasympathetic nervous system. Second, LF power spectrum graph 198 depicts that there is a strengthening in the LF power after perturbation corresponding to the slower response of sympathetic nervous system. Third, HF power spectrum graph 200, which reflects only the functioning of the parasympathetic nervous system, depicts that HF power is attenuated after the perturbation. And fourth, the LF/HF sympathovagal balance ratio graph 202 depicts that the contribution of LF power is greater after the perturbation confirming the known functioning of the ANS during the change of posture.

It can therefore be appreciated that apparatus 100 provides time dependent evaluation of the functioning of the ANS which will be useful in the clinical interpretation of a wide range of clinical conditions including, autonomic changes relative to fainting spells such as vasovagal syncope, tilt test, autonomic failure, autonomic imbalance, diabetic neuropathy, cardiac ischemic changes, effects of drugs interfering with autonomic or ischemic changes, angioplasty effects on autonomic control, early detection of hypertension. Furthermore, apparatus 100 can be used for all kinds of autonomic tests such as: hand grip, cold pressor test, vagal maneuvers such as Oculocardiac Reflex or Diving Response, valsalva maneuver and the like. It can also be appreciated that apparatus 100 can provide time dependent power spectrum analysis of a wide range of other physiological signals in a similar fashion.

While the invention has been described with respect to a limited number of embodiments, it will be appreciated that many variations, modifications and other applications of the invention may be made.

What is claimed is:

1. An apparatus for time dependent power spectrum analysis of a physiological signal modulated by the autonomic nervous system, the apparatus comprising:
   (a) a sensor for picking up a physiological signal modulated by the autonomic nervous system;
   (b) frequency selection apparatus for selecting at least one frequency inherent to said signal;
   (c) a selective windowed time-frequency analysis processor for determining the power spectrum of said physiological signal within a window along said signal for said at least one frequency, said processor calculates the duration of said window as a function of said at least one frequency, thereby enabling the analysis of signals under non-steady state conditions; and
   (d) output apparatus for providing information associated with the functioning of the autonomic nervous system as provided by the power spectrum of the physiological signal.

2. The apparatus as in claim 1, wherein said sensor comprises one of the following: an ECG recorder, a respiratory monitor, a blood pressure transducer, a Doppler flow meter, a tachometer, a finger plesthysmograph, a skin resistance galvanometer, cardiovascular monitoring equipment.

3. The apparatus as in claim 1, wherein said window has an aperture selected from one of the following: a rectangular aperture, a Hamming aperture, a Hanning aperture, a Blackman aperture, a Gaussian window, a Lorentzian window, a sinc window, a power of a sine window and a power of a cosine window.

4. The apparatus as in claim 1, further comprising frequency selection apparatus for determining the frequency resolution of the apparatus.

5. The apparatus as in claim 1, further comprising timing selection apparatus for determining the time resolution of the apparatus.

6. The apparatus as in claim 1, further comprising a physiological signal selector for selecting the type of physiological signal picked up said sensor.

7. The apparatus as in claim 1, further comprising a type of perturbation selector for selecting the type of perturbation to be applied to a subject under investigation.

8. The apparatus as in claim 1, further comprising at least one frequency register for determining the range of frequency outputted on said output apparatus.

9. The apparatus as in claim 1, further comprising at least one timer for determining the onset and termination of the time dependent power spectrum of the physiological signal outputted on said output apparatus.

10. The apparatus as in claim 1, further comprising a detrending filter deployed between said sensor and said selective windowed time-frequency analysis processor.

11. The apparatus as in claim 1, wherein said selective windowed time-frequency analysis processor comprises a Wavelet processor.

12. The apparatus as in claim 11, further comprising a prototype function selector for selecting a prototype function applied by said Wavelet processor.

13. The apparatus as in claim 11, further comprising a scale parameters selector for selecting scale parameters applied by said Wavelet processor.

14. The apparatus as in claim 11, further comprising a shift parameters selector for selecting shift parameters applied by said Wavelet processor.

15. The apparatus as in claim 1, wherein said selective windowed time-frequency analysis processor comprises a selective discrete spectral transform algorithm processor.

16. The apparatus as in claim 15, further comprising a spectral transform selector for selecting a transform selected from one of the following: the Fourier transform, the Haar transform, the Hartley transform, the sine transform, the cosine transform, and the Hadamard transform.

17. The apparatus as in claim 15, further comprising a window duration selector for selecting the duration of said window.

18. The apparatus as in claim 15, further comprising a window aperture selector for selecting the aperture of said window.

19. The apparatus as in claim 15, further comprising a number of points selector for selecting the number of data points within said window.

20. The apparatus as in claim 15, further comprising a decimation technique selector for selecting the decimation technique applied by said selective discrete spectral transform analysis processor.

21. A method of time dependent power spectrum analysis of a physiological signal modulated by the autonomic nervous system, the method comprising the steps of:
   (a) picking up a physiological signal modulated by the autonomic nervous system;
   (b) selecting at least one frequency inherent to the signal;
   (c) determining the power spectrum of the physiological signal within a window along said signal for the at least one frequency by using a selective windowed time frequency analysis processor, wherein said processor calculates the duration of said window as a function of said at least one frequency, thereby enabling the analysis of signals under non-steady state conditions; and
   (d) providing information associated with the functioning of the autonomic nervous system as provided by the power spectrum of the physiological signal.

22. An apparatus for time dependent power spectrum analysis of a physiological signal, the apparatus comprising:
   (a) a sensor for picking up a physiological signal;
   (b) a frequency selector electrically connected to said sensor for selecting at least one frequency inherent to said signal;
   (c) window generating apparatus electrically connected to said frequency selector for generating a window along said signal, the duration of said window being substantially inversely related to said at least one frequency;
   (d) decimation apparatus electrically connected to said sensor and said window generating apparatus for providing data points within said window;
   (e) spectral transform apparatus electrically connected to said decimation apparatus for determining the power spectrum of said signal within said window for said at least one frequency; and
   (f) output apparatus electrically connected to said spectral transform apparatus for providing information associated with time dependent power spectrum of said signal.

23. The apparatus as in claim 22, wherein said sensor comprises one of the following: an ECG recorder, a respiratory monitor, a finger plesthysmograph, a Doppler flow meter, a tachometer, a blood pressure transducer, a skin resistance galvanometer, an EEG monitor, an EMG monitor.

24. The apparatus as in claim 22, wherein said window having an aperture selected from one of the following: a rectangular aperture, a Hamming aperture, a Hanning aperture, a Blackman aperture, a Gaussian window, a Lorentzian window, a sinc window, a power of a sine window, and a power of a cosine window.

25. The apparatus as in claim 22, further comprising frequency selection apparatus for determining the frequency resolution of the apparatus.

26. The apparatus as in claim 22, further comprising timing selection apparatus for determining the time resolution of the apparatus.

27. The apparatus as in claim 22, further comprising a physiological signal selector for selecting the type of physiological signal picked up said signal.

28. The apparatus as in claim 22, further comprising a type of perturbation selector for selecting the type of perturbation to be applied to a subject under investigation.

29. The apparatus as in claim 22, further comprising at least one frequency register for determining the range of frequency outputted on said output apparatus.

30. The apparatus as in claim 22, further comprising at least one timer for determining the onset and termination of the time dependent power spectrum of the physiological signal outputted on said output apparatus.

31. The apparatus as in claim 22, further comprising a detrending filter deployed between said sensor and said selective windowed time-frequency analysis processor.

32. The apparatus as in claim 22, further comprising a spectral transform selector for selecting a transform selected from one of the following: the Fourier transform, the Haar transform, the Hartley transform, the sine transform, the cosine transform, and the Hadamard transform.

33. The apparatus as in claim 22, further comprising a window duration selector for selecting the duration of said window.

34. The apparatus as in claim 22, further comprising a window aperture selector for selecting the aperture of said window.

35. The apparatus as in claim 22, further comprising a number of points selector for selecting the number of data points within said window.

36. The apparatus as in claim 22, further comprising a decimation technique selector for selecting the decimation technique applied by said selective discrete spectral transform analysis processor.

37. A method of time dependent power spectrum analysis of a physiological signal, the method comprising the steps of:
   (a) picking up a physiological signal;
   (b) selecting at least one frequency inherent to the signal;
   (c) generating a window along the signal by using a window generating apparatus, said window generating apparatus calculates the duration of the window to be substantially inversely related to the at least one frequency so as to enable the analysis of signals under non-steady state conditions;

(d) providing data points within the window;

(e) determining the power spectrum of the signal within the window for the at least one frequency; and (f) providing information associated with time dependent power spectrum of the signal.

38. An apparatus for time dependent power spectrum analysis of a physiological signal modulated by the autonomic nervous system, the apparatus comprising:

(a) a sensor for picking up a physiological signal modulated by the autonomic nervous system;

(b) frequency selection apparatus for selecting at least one frequency inherent to said signal;

(c) a selective windowed time-frequency analysis processor for determining the power spectrum of said physiological signal within a window along said signal for said at least one frequency, said window has an aperture selected from one of the following: a rectangular aperture, a Hamming aperture, a Hanning aperture, a Blackman aperture, a Gaussian window, a Lorentzian window, a sinc window, a power of a sine window and a power of a cosine window; and (d) output apparatus for providing information associated with the functioning of the autonomic nervous system as provided by the power spectrum of the physiological signal.

39. An apparatus for time dependent power spectrum analysis of a physiological signal modulated by the autonomic nervous system, the apparatus comprising:

(a) a sensor for picking up a physiological signal modulated by the autonomic nervous system;

(b) frequency selection apparatus for selecting at least one frequency inherent to said signal;

(c) a selective windowed time-frequency analysis processor for determining the power spectrum of said physiological signal within a window along said signal for said at least one frequency, said selective windowed time-frequency analysis processor comprises a Wavelet processor; and (d) output apparatus for providing information associated with the functioning of the autonomic nervous system as provided by the power spectrum of the physiological signal.

40. The apparatus of claim 39, further comprising a prototype function selector for selecting a prototype function applied by said Wavelet processor.

41. The apparatus of claim 39, further comprising a scale parameters selector for selecting scale parameters applied by said Wavelet processor.

42. The apparatus as in claim 39, further comprising a shift parameters selector for selecting shift parameters applied by said Wavelet processor.

43. An apparatus for time dependent power spectrum analysis of a physiological signal modulated by the autonomic nervous system, the apparatus comprising:

(a) a sensor for picking up a physiological signal modulated by the autonomic nervous system;

(b) a physiological signal selector electrically connected to said sensor for selecting the type of physiological signal picked up by said sensor;

(c) frequency selection apparatus for selecting at least one frequency inherent to said signal;

(d) a selective windowed time-frequency analysis processor for determining the power spectrum of said physiological signal within a window along said signal for said at least one frequency; and (e) output apparatus for providing information associated with the functioning of the autonomic nervous system as provided by the power spectrum of the physiological signal.

44. An apparatus for time dependent power spectrum analysis of a physiological signal modulated by the autonomic nervous system, the apparatus comprising:

(a) a sensor for picking up a physiological signal modulated by the autonomic nervous system;

(b) frequency selection apparatus for selecting at least one frequency inherent to said signal;

(c) a selective windowed time-frequency analysis processor for determining the power spectrum of said physiological signal within a window along said signal for said at least one frequency;

(d) output apparatus for providing information associated with the functioning of the autonomic nervous system as provided by the power spectrum of the physiological signal; and (e) a type of perturbation selector for selecting the type of perturbation to be applied to a subject under investigation.

45. An apparatus for time dependent power spectrum analysis of a physiological signal modulated by the autonomic nervous system, the apparatus comprising:

(a) a sensor for picking up a physiological signal modulated by the autonomic nervous system;

(b) frequency selection apparatus for selecting at least one frequency inherent to said signal;

(c) a selective windowed time-frequency analysis processor for determining the power spectrum of said physiological signal within a window along said signal for said at least one frequency;

(d) output apparatus for providing information associated with the functioning of the autonomic nervous system as provided by the power spectrum of the physiological signal; and (e) a detrending filter deployed between said sensor and said selective windowed time-frequency analysis processor.

46. An apparatus for time dependent power spectrum analysis of a physiological signal modulated by the autonomic nervous system, the apparatus comprising:

(a) a sensor for picking up a physiological signal modulated by the autonomic nervous system;

(b) frequency selection apparatus for selecting at least one frequency inherent to said signal;

(c) a selective windowed time-frequency analysis processor for determining the power spectrum of said physiological signal within a window along said signal for said at least one frequency, said selective windowed time-frequency analysis processor comprises a selective discrete spectral transform algorithm processor;

(d) a window duration selector for selecting the duration of said window;

(e) output apparatus for providing information associated with the functioning of the autonomic nervous system as provided by the power spectrum of the physiological signal.

47. The apparatus of claim 46, further comprising a spectral transform selector for selecting a transform selected from one of the following: the Fourier transform, the Haar transform, the Hartley transform, the sine transform, the cosine transform, and the Hadamard transform.

48. The apparatus of claim 46, further comprising a window aperture selector for selecting the aperture of said window.

49. The apparatus of claim 46, further comprising a number of points selector for selecting the number of data points within said window.

50. The apparatus of claim 46, further comprising a decimation technique selector for selecting the decimation technique applied by said selective discrete spectral transform analysis processor.

* * * * *